(12) United States Patent
Silverstein et al.

(10) Patent No.: US 11,443,848 B2
(45) Date of Patent: Sep. 13, 2022

(54) SYSTEM AND METHOD FOR PROVIDING NOTIFICATIONS TO A USER BASED UPON THE LOCATION OF THE USER

(71) Applicant: Amaze PBC, Denver, CO (US)

(72) Inventors: David Mark Silverstein, Longmont, CO (US); Felix Weitzman, Conifer, CO (US)

(73) Assignee: Amaze PBC, Denver, CO (US)

( * ) Notice: Subject to any disclaimer, the term of this patent is extended or adjusted under 35 U.S.C. 154(b) by 346 days.

(21) Appl. No.: 16/714,758

(22) Filed: Dec. 15, 2019

(65) Prior Publication Data

US 2021/0183502 A1    Jun. 17, 2021

(51) Int. Cl.
   *G16H 40/20* (2018.01)
   *H04W 4/021* (2018.01)
   *H04L 51/224* (2022.01)

(52) U.S. Cl.
   CPC .......... *G16H 40/20* (2018.01); *H04L 51/224* (2022.05); *H04W 4/021* (2013.01)

(58) Field of Classification Search
   CPC ........ G16H 40/20; H04L 51/24; H04W 4/021
   See application file for complete search history.

(56) References Cited

U.S. PATENT DOCUMENTS

| | | |
|---|---|---|
| 7,925,519 B2 | 4/2011 | Greene et al. |
| 8,010,717 B2 | 8/2011 | Evans et al. |
| 8,504,386 B2 | 8/2013 | Manning et al. |
| 8,554,195 B2 | 10/2013 | Rao |
| 8,600,008 B2 | 12/2013 | Kraus et al. |
| 8,924,238 B1 | 12/2014 | Nidy et al. |
| 9,886,547 B2 | 2/2018 | Baniameri et al. |
| 9,924,315 B1 | 3/2018 | Cornwall et al. |
| 10,178,537 B2 | 1/2019 | Rauner |
| 10,492,023 B1 | 11/2019 | Gurin |
| 10,650,380 B1 * | 5/2020 | Harris, Sr. ........... G06Q 20/401 |
| 2002/0077865 A1 * | 6/2002 | Sullivan ................. G16H 10/60 705/3 |
| 2002/0178030 A1 * | 11/2002 | Loeb ...................... G16H 70/20 705/2 |

(Continued)

FOREIGN PATENT DOCUMENTS

| | | | | |
|---|---|---|---|---|
| KR | 20200106276 A | * | 9/2020 | |
| WO | WO-2013025520 A2 | * | 2/2013 | ............ A61J 7/0481 |

*Primary Examiner* — Chris Parry
*Assistant Examiner* — Abderrahmen Chouat
(74) *Attorney, Agent, or Firm* — Brett A. Schenck

(57) ABSTRACT

This application provides a computer-implemented method for providing notifications. The method includes creating and storing a geofenced area associated with a mobile device and a location that has a healthcare facility in a data store and outputting a notification to the mobile device when the mobile device is within the geofenced area. The notification may include that the location offers at least one healthcare service that can be received on an unscheduled basis, where in the facility that the at least one healthcare service is offered, whether or not the healthcare service is covered by a patient's insurance, the cost of the healthcare service, the out-of-pocket cost by the patient of the healthcare service, wait time at the facility for the healthcare service, and when the patient should not receive the healthcare service for other medical reasons.

19 Claims, 10 Drawing Sheets

(56) References Cited

U.S. PATENT DOCUMENTS

| | | | |
|---|---|---|---|
| 2008/0275737 A1* | 11/2008 | Gentry | G06Q 40/08 |
| | | | 705/3 |
| 2014/0372134 A1* | 12/2014 | Dahr | G06Q 10/10 |
| | | | 705/2 |
| 2015/0213414 A1* | 7/2015 | Zuckerman | G06Q 10/1095 |
| | | | 705/7.19 |
| 2015/0371350 A1* | 12/2015 | Zebarjadi | G16H 40/20 |
| | | | 705/2 |
| 2018/0089387 A1 | 3/2018 | Swank | |
| 2018/0166176 A1 | 6/2018 | Flippen et al. | |
| 2019/0043613 A1 | 2/2019 | Gallagher et al. | |
| 2019/0088106 A1 | 3/2019 | Grundstrom | |
| 2019/0237187 A1 | 8/2019 | Carter et al. | |
| 2020/0092389 A1* | 3/2020 | Conolly | H04W 4/23 |
| 2020/0125659 A1* | 4/2020 | Brisimi | G06N 5/025 |
| 2020/0246543 A1* | 8/2020 | Sadeghzadeh | A61B 5/7435 |

* cited by examiner

SYSTEM AND METHOD FOR PROVIDING NOTIFICATIONS TO A USER BASED UPON THE LOCATION OF THE USER

FIELD

This application relates to a system and method for providing notifications to a user based upon the user's location.

BACKGROUND

Often when a person travels from place to place there are locations along the way that offer healthcare services that do not need to be scheduled in advance. The person may have certain healthcare services that are due or desired and these locations may offer those services to people on an unscheduled basis. The person may also want further information about the facility offering the services as related to his or her healthcare needs. Failure to learn that a useful medical facility was available may be a lost opportunity by both the patient and the provider of the healthcare services for the patient to conveniently take care of their healthcare services at these locations.

SUMMARY

This application addresses the above-mentioned problem. In one aspect of this application, a computer-implemented method for providing notifications and communication based on a patient entering into a geofenced area around a facility that offers unscheduled healthcare services is provided. The method includes operations performed by at least one computer processor. These operations include a) creating a geofenced area associated with a mobile device and a location that has the facility, wherein the patient is associated with the mobile device, b) storing the geofenced area in a data store, c) determining when the mobile device has crossed or entered the geofenced area, d) sending a notification to or retrieving the notification from the mobile device, wherein the notification includes one of or any combination of: that the location offers at least one healthcare service that can be received on an unscheduled basis, where in the facility that the at least one healthcare service is offered, whether or not the at least one healthcare service is covered by the patient's insurance, the cost of the at least one healthcare service, the out-of-pocket cost by the patient of the at least one healthcare service, wait time at the facility for the at least one healthcare service, and when the patient should not receive the at least one healthcare service for other medical reasons, and e) outputting the notification to the mobile device when the location data of the mobile device is determined to be within the geofenced area that corresponds to the facility.

In another aspect of this application, a computer-implemented method for providing notifications is provided. The method includes operations performed by at least one computer processor. These operations include a) creating a geofenced area associated with a mobile device and a location that has the facility, wherein the patient is associated with the mobile device, b) storing the geofenced area in a data store, c) determining when the mobile device has crossed or entered the geofenced area, d) sending a notification to or retrieving the notification from the mobile device, wherein the notification includes a message that the particular healthcare service is due for the patient, wherein the notification further includes prompting the patient to request or place an order for the particular healthcare service, and e) outputting the notification to the mobile device when the location data of the mobile device is determined to be within the geofenced area that corresponds to the facility.

Further embodiments of the disclosed a system and method for providing notifications to a user based upon the user's location will become apparent from the following detailed description, the accompanying drawings and the appended claims.

DETAILED DESCRIPTION

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

As used herein, the terms "component" and "system" are intended to encompass hardware, software, or a combination of hardware and software. Thus, for example, a system or component may be a process, a process executing on a processor, or a processor. Additionally, a component or system may be localized on a single device or distributed across several devices.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

Figure 1:
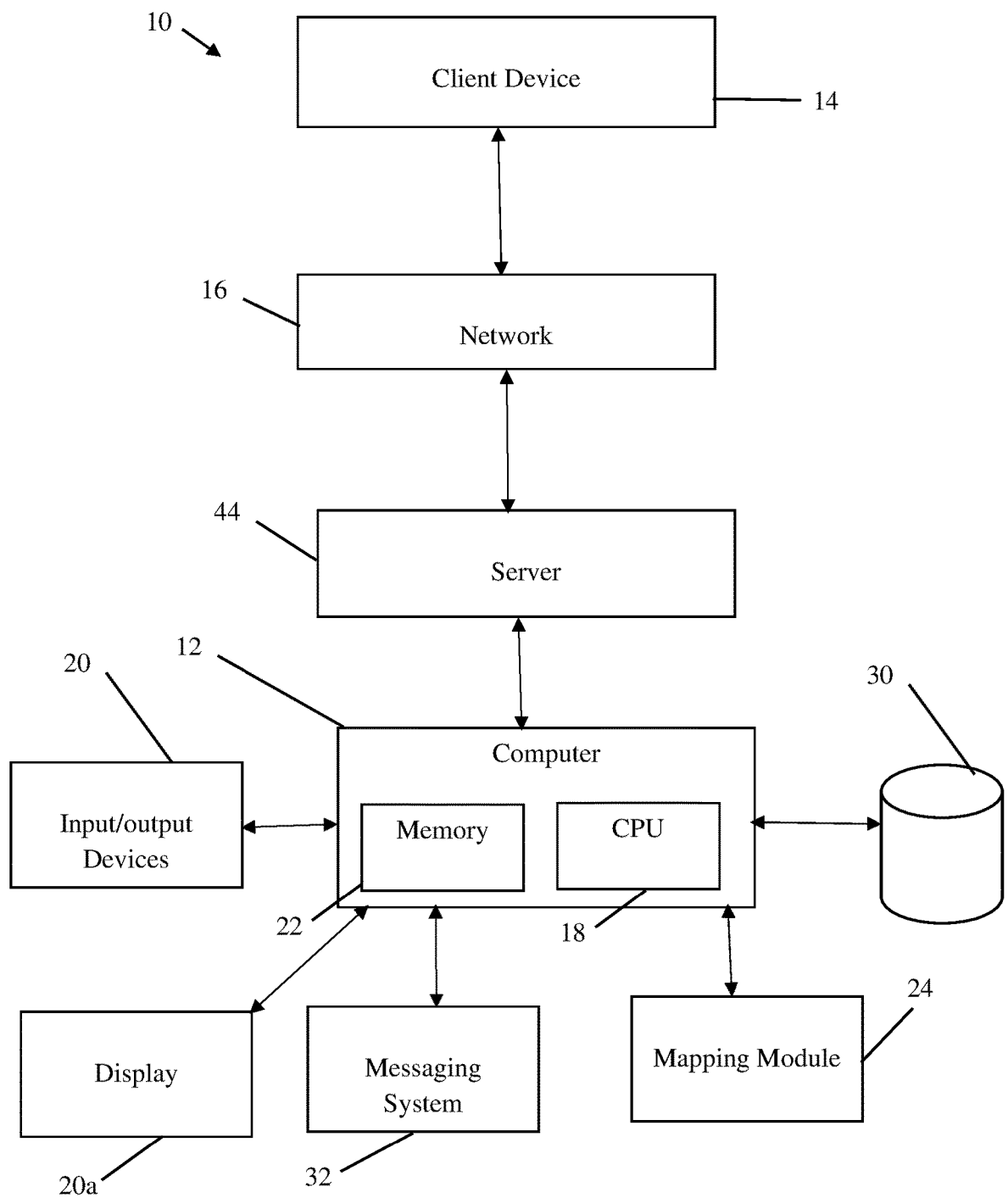
FIG. 1 is a block diagram of the components of the system according to one embodiment of the present invention.

FIG. 1 shows a block diagram of a system 10 that provides notifications to a patient or person as he or she approaches a facility that offers unscheduled healthcare services or one or more types of healthcare services according to the present invention. The healthcare services may also be preventative healthcare services. The system 10 may include a computer 12 and a client device 14 such as a mobile device. The components may each be connected and placed in communication with one another over a computer network 16. Embodiments of the network 16 may be constructed using wired or wireless connections between each hardware component connected to the network 16.

The computer 12 may generally comprise a processor 18, otherwise referred to as a central processing unit (CPU), input/output devices 20 such as a display 20a, keyboard, printer etc. coupled to the processor 18, and memory device 22. The processor 18 may perform computations and control the functions of the computer 12, including executing instructions included in the computer code for tools and programs for creating geofenced areas and triggering a geofence notification, in the manner prescribed by the embodiments of the disclosure using the components, wherein the instructions of the computer code may be executed by the processor 18 via memory device 22. The computer code may include software or program instructions that may implement one or more algorithms for implementing the methods for providing a geofence notification. The processor 18 executes the computer code. The processor 18 may include a single processing unit, or may be distributed across one or more processing units in one or more locations (e.g., on a client and server).

The memory device 22 may include input data. The input data includes any inputs required by the computer code. The display 20a displays output from the computer code. The memory device 22 may be used as a computer usable storage medium (or program storage device) having a computer readable program embodied therein and/or having other data stored therein, wherein the computer readable program comprises the computer. The computer 12 may be accessed by a medical professional such as a doctor, physician assistant, nurse practitioner, or other medically or non-medically trained service provider who may provide information, service or support to the patient.

The system may include a mapping module 24. The term "module" may refer to a hardware based module, software based module or a module may be a combination of hardware and software resources. A module (whether hardware, software, or a combination thereof) may be designed to implement or execute one or more particular functions, tasks or routines of the system. Embodiments of hardware based modules may include self-contained components such as chipsets, specialized circuitry and one or more memory devices. A software-based module may be part of a program code or linked to program code containing specific programmed instructions loaded in a memory device.

The mapping module 24 may create one or more geofenced areas such as one geofenced area 26 (FIG. 6) associated with a healthcare facility or a facility 31 that offers preventative healthcare services based on data in the system. The healthcare facility may also offer healthcare service that can be received on an unscheduled basis. The geofenced area 26 may also be associated with the mobile device 14.

Figure 7:
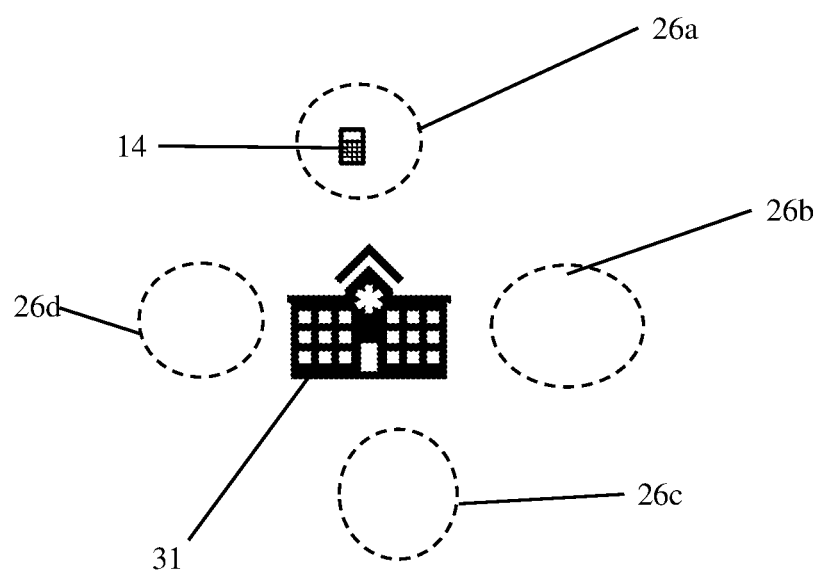
FIG. 7 is a schematic view of a healthcare facility with a first group of geofenced areas associated with a healthcare facility and illustrating a mobile device located within one of the geofenced areas according to the present invention.

The mapping module 24 may alternatively create a first group of geofenced areas 26a-26d (FIG. 7) based on data in the system. The first group of geofenced areas 26a-26d may be created to correspond to or associate with the facility 31 as shown in FIG. 7 and with the mobile device 14. Each geofenced area of the first group may be entered from directions or ways that differ from each of the other one or more geofenced areas in the first group of geofenced areas 26a-26d. For example, large supermarket, or a hospital emergency room on a hospital campus may have several geofenced areas associated with it, since one large geofenced area encircling the emergency room would not work, because there may be too many false triggers for people going to the hospital for other purposes. Further, there may be cases where there are one or more parking lots, driveways or entrances that are exclusively for the emergency room, so these parking lots and other such location would be associated with a geofenced area for the emergency room. This would also allow for an earlier detection and notification compared with just having a small geofenced area around the emergency room.

In another example, a large supermarket campus may have several geofenced areas associated with it, since one large geofenced area encircling the location providing the healthcare services room would not work, because there may be too many false triggers for people going to the supermarket for other purposes. Further, there may be cases where there are one or more parking lots, driveways or entrances that are exclusively for the location providing the healthcare services, so these parking lots and other such location would be associated with a geofenced area for the emergency room. Additionally, the geofenced area, which may be defined by other location services such as wifi hotspots or beacons, may be inside a building versus outside. For example, the geofenced area could be a particular store or clinic inside a shopping mall or a clinic inside of a department store.

The mapping module 24 may receive geofence configuration data defining the properties of each geofenced area. The geofence configuration data may include data defining each geofences' name, location, and size or virtual boundary limits (i.e. longitude, latitude and radius, proximity, or detection of other location determining digital signals). The geofencing configured may comprise a defined geographic boundary area (a radius around an address, geo position coordinates, or other specified location or a geometric boundary such as a geofence or a proximity (distance) from a specific location.

The mapping module 24 may create interruption conditions based on data in the system 10 to prevent outputting messages to the client device 14 when the location data of the client device 14 is determined to be within a geofenced area. This avoids unnecessary triggers. One interruption condition may include prior to outputting the notification to the mobile device, determining if the patient had the at least one healthcare service within a predetermined time ago and preventing the outputting of the notification upon determining that the patient had the at least one healthcare service within a predetermined time ago. Another interruption condition may include prior to outputting the notification to the mobile device, determining that the at least one healthcare service should not be provided to the patient and preventing the outputting of the notification upon determining that the at least one healthcare service should not be provided to the patient. Determining that the at least one healthcare service should not be provided to the patient may be based on the medical history of the patient. Determining that the at least one healthcare service should not be provided to the patient may also be based on one or more insurance claims of the patient.

Another interruption condition may include prior to outputting the notification to the mobile device, determining that the preference of the patient is to not output the notification and preventing the outputting of the notification upon determining that the preference of the patient is to not output the notification. Another interruption condition may include prior to outputting the notification to the mobile device, determining that the at least one healthcare service is not in the insurance network of the patient and preventing the outputting of the notification upon determining that the at least one healthcare service is not in the insurance network of the patient. Another interruption condition may include prior to outputting the notification to the mobile device, determining that the cost of the at least one healthcare service is not available or more than a predetermined amount at the facility and preventing the outputting of the notification upon determining that the cost of the at least one healthcare service is not available or more than a predetermined amount at the facility. Another interruption condition may include prior to outputting the notification to the mobile device, determining that the quality of the at least one healthcare service at the facility is not adequate and preventing the outputting of the notification upon determining that the quality of the at least one healthcare service at the facility is not adequate. This information may be stored in a data store 30, as well as from location data from his or her client device 14.

Other interruption conditions may be based on information about where a patient or person associated with the client device 14 works, lives, and/or where or when his or her daily activities (e.g. commuting, shopping, walking, running, bike-riding, etc.) are performed. This information may come from his or her addresses (home, work, gym, etc.) stored in a data store 30, as well as from location data from his or her client device 14. For example, an interruption condition may be created for the workplace of a person associated with the client device 14 and activated only during the working hours of the person if the workplace is a healthcare facility. A person may operate the computer 12 to enter the data to create the interruption condition. The interruption conditions may be based on one or more predetermined dates and times when the location data of the mobile device is determined to be within the geofenced area. The interruption conditions may also be based on determining that the patient frequently passes through the geofenced area en route to another location. The interruption conditions may also be based on determining that the patient frequents the geofenced area for purposes unrelated to receiving healthcare services.

The system 10 may include a messaging system 32. The messaging system 32 may perform the functions, tasks and services of the system 10 directed toward creating notifications or messages and notification events associated with the system such as notifications to the client device 14. The message system may send a one or more notifications upon the occurrence of one or more of the programmed transitions. For example, when a client device 14 breaches a virtual boundary of a geofenced area (entering or exiting), a geofence notification may be transmitted to the client device 14.

Figure 2:
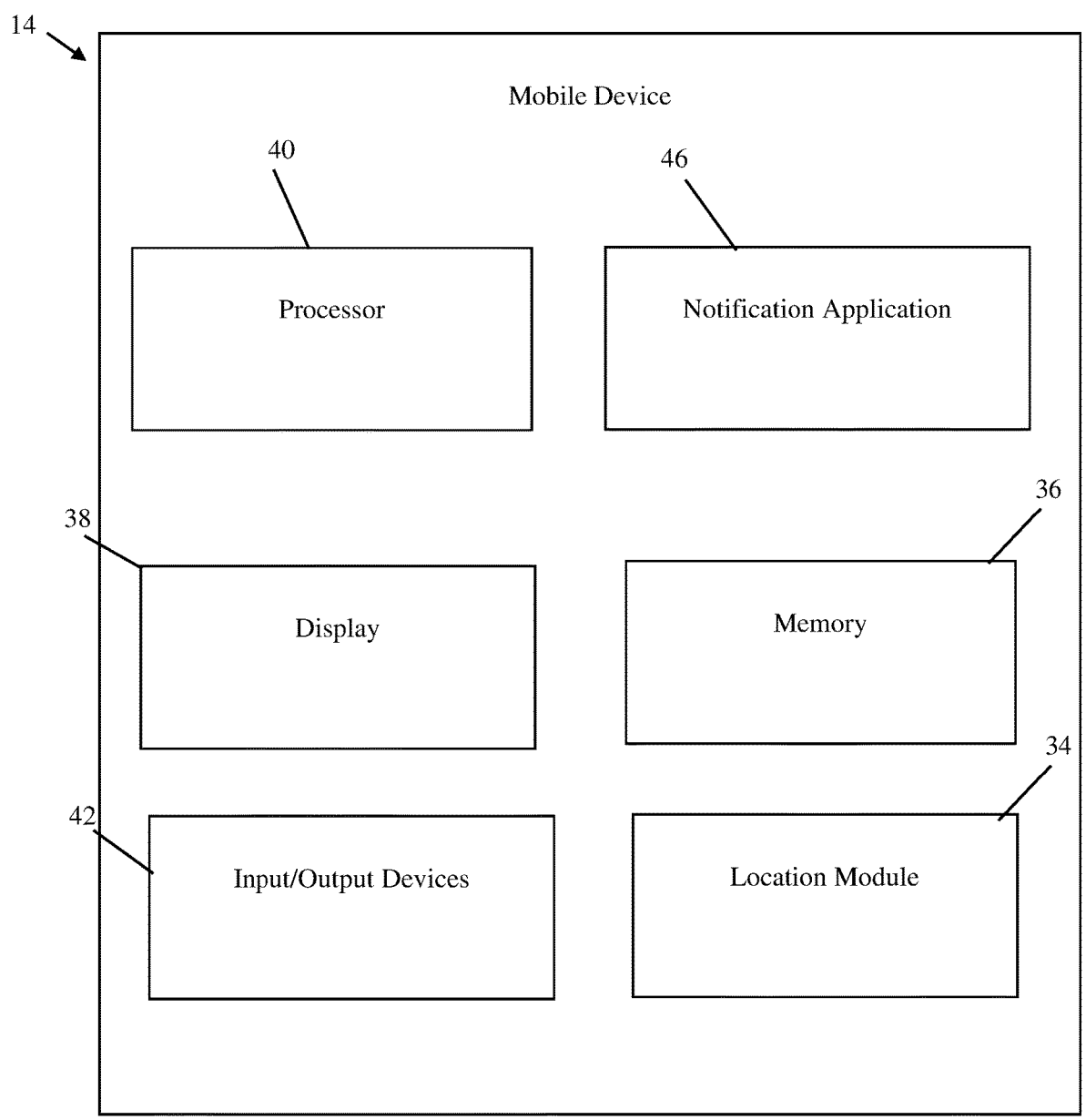
FIG. 2 is a block diagram of the client device and related elements according to the system of FIG. 1.

The system 10 may further comprise a location module 34 associated with the client device 14 as illustrated in FIG. 2.

The location module 34 detects, processes and communicates the location of the client device associated with the user. Location sensing technology may include but is limited to global positioning systems (GPS), Wi-Fi, Bluetooth, 3G, 4G, 5G, 6G, 7G cellular technology, near field communications, radio frequency identification (RFID), beacons, and any other location identifying signal. The location module 34 may be comprised of hardware and/or software capable of utilizing a positioning system to pinpoint the current location of the client device 14 and/or previously stored locations of the client device 14 that may be saved in a memory device 36 or data store 30. The location module 34 may include a transmitter, receiver and/or transceiver for receiving location data from a positioning system or broadcasting the location data to the system 10. The location module 34 may save, store and update one or more sets of location data to a memory device onboard the location module 34 or, the location module 34 may store the location information to the memory device 36 or the data store 30. The location module 34 may include any sort of system that informs the mobile device of its geolocation including, but not limited to, the Global Positioning System of satellites circling the Earth.

With continued reference to FIG. 2, the client device 14 may be a portable device such as a mobile device in operative communication with each other. The mobile device 14 may be any computing device small enough to hold and operate in the hand. The mobile device 14 may comprise a display 38 having a flat screen interface that provides a touchscreen interface with digital buttons and keyboard, and/or physical buttons along with a physical keyboard. The mobile device 14 may connect to the Internet and interconnect with other devices such as car entertainment systems or headsets via Wi-Fi, Bluetooth, cellular networks or near field communication (NFC). The flat screen interface may be an LCD flat screen interface, an OLED flatscreen interface, or other suitable type of flat screen interface. Alternatively, the display 38 may being the form of a hologram. The mobile device 14 may be a cell phone, smart phone, smart watch, tablet, PDA, laptop, notebook or other suitable portable or mobile device. The mobile device 14 is configured to detect its location and hence the location of a user using the mobile device 14 or other person near the mobile device 14.

The mobile device 14 includes one or more processors 40 and the memory device 36. The memory device 36 may contain a user identification module that may in turn contain a user identifier and/or user information. The user identifier may be a unique number or code that uniquely identifies the user of the mobile device. The mobile device 14 may also include input/output devices 42 such as a camera capable of taking still or video pictures and have the capability to make video calls (see FIG. 5). An antenna in the mobile device may send and receive wireless signals from sources such as the radio antenna and satellite. The antenna may, in some implementations, communicate directly with the server such as by exchanging wireless signals. The mobile device 14 may further comprise other input/output devices 42, such as a microphone and a speaker used, for example, in an implementation in which the mobile device 14 functions as a telephone. In some implementations, the mobile device 14 may also include a calendar/clock and a network interface. The calendar/clock may calculate time, date, and other data that can be derived from time data and date data.

The mobile device 14 includes applications that manage interactions between a server 44 (FIG. 1) and the mobile device 14. The applications may include a notification application 46. The data store 30 associated with the system 10 may contain data on healthcare facilities and their type. For example, the type of healthcare facility stored in the data store 30 may be a hospital, free-standing emergency, urgent care, or walk-in clinic. One or more of the healthcare facilities stored in the data store 30 may be associated with the patient associated with the mobile device 14. For example, the healthcare facility may be in the patient's insurance network with this data stored in the data store 30.

The data store 30 may also store personal and medical information about the patient in the form of a record. This and other information may be made available to the patient or other person via the mobile device 14 or computer 12. The data store 30 may store an address associated with a property and a geofenced area associated with the property. The data store 30 also may store all the mobile phone numbers of the smartphones which have the notification application 46 installed. The installed notification application 46 has the geofence information so that the mobile device 14 knows, using GPS technology, whether it is inside or outside the geofenced area.

The data store 30 may store information on patient(s) or person(s) associated with the mobile device related to their medical history to speed the process of receiving the services of the healthcare facility, lists of medical questions to ask, ratings on the facility being entered or the medical professionals practicing at that facility, information about whether the facility and\or medical providers participate in their insurance network, the medical providers practicing at the healthcare facility, wait times at the healthcare facility, and the proximity to other healthcare facilities and information about the prices of the facility or providers. This data may be displayed on the display 38 of the mobile device 14. The data store 30 may store the interruption conditions for preventing the outputting of the notification when the location data of the mobile device is determined to be within the geofenced area that are created using the mapping module 24 in exemplary embodiments.

The data store 30 may store information as to where in the facility that the at least one healthcare service is offered that can be received on an unscheduled basis, whether or not the healthcare service is covered by the patient's insurance, the cost of the healthcare service, the out-of-pocket cost by the patient of the healthcare service, and when the patient should not receive the healthcare service for other medical reasons. The data store may store information as to when a particular healthcare service is due for the patient. For example, the data store may store information as to when the patient's blood pressure should be tested, when an eye examination should be performed on the patient, and when lab work for the patient's physical examination is due. The data store may also store information as to whether the facility 31 offers the particular healthcare service such as lab work, blood pressure testing, and eye examination.

Figure 4:
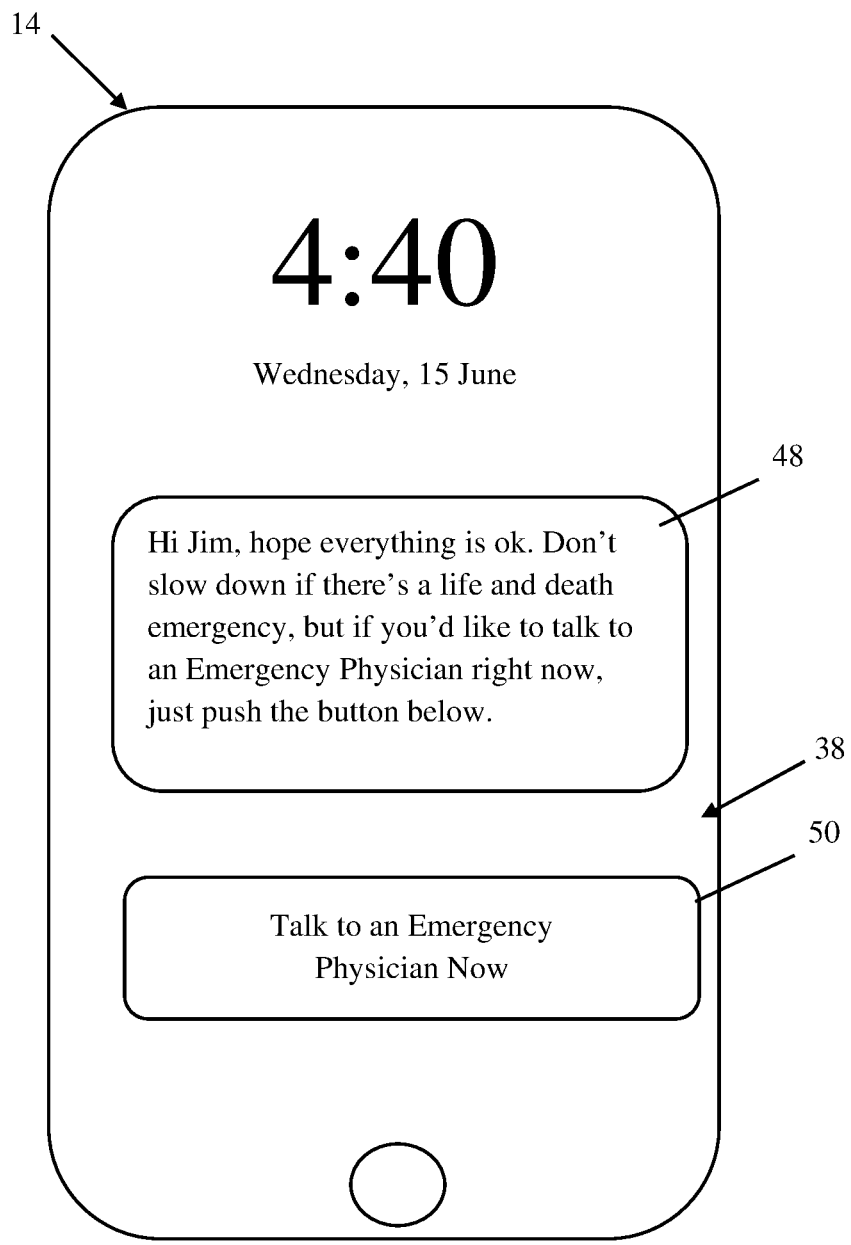
FIG. 4 is a schematic front view of mobile device displaying a message and message button on the display of the mobile device of the system according to FIG. 1.

The system 10 may identify a type of healthcare facility and then map or link that type with a certain message. The message may include a button. For example, an emergency healthcare facility may be linked with a notification or message 48 and a message button 50 for making video calls displayed on the display 38 of the mobile device 14 as shown in FIG. 4. The computer 12 may display on its display 20a the above-mentioned information corresponding to the healthcare facilities or the patient associated with the client device or other information for the medical professional to access.

The computer 12 and mobile device 14 may communicate with the server 44 via the internet over the network 16 as illustrated in FIG. 1. The network may include any one or combination of multiple different types of networks, such as cable networks, local area networks, personal area networks, wide area networks, the Internet, wireless networks, ad hoc networks, mesh networks, and/or the like. In some implementations the satellite and/or the radio antenna may provide network connectivity to the mobile device as well as provide geolocation. For example, the radio antenna may provide network access to the mobile device according to the International Mobile Telecommunications-2000 standards (3G network) or the International Mobile Telecommunications Advanced standards (4G network) or the 5G or 6G networks. Other implementations may include one source of geolocation data such as the satellite and a separate source of network connectivity such as a Wi-Fi hotspot. The server may house or otherwise have a connection to multiple data stores including user information and/or other data stores. The server 44 and data stores can be stored where desired, for example in a cloud.

Generally, the user information contains information about the user associated with the mobile device 14. The notification application 46 is operatively connected to the server 44 which is connected to the data store 30. The notification application 46 has notifications and messages associated with different types of conditions. The messages may include buttons for the user to operate. For example, FIG. 4 shows a notification message 48 and message button 50 for making video calls generated by the messaging system 32 when the mobile device 14 enters a geofenced area associated with a free-standing emergency facility. The notifications or messages may be stored in the memory 36 of the mobile device 14 or in the data store 30. One or more notifications may include information about one of or any combination of: that the location offers at least one healthcare service that can be received on an unscheduled basis, where in the facility that the at least one healthcare service is offered, whether or not the healthcare service is covered by the patient's insurance, the cost of the healthcare service, the out-of-pocket cost by the patient of the healthcare service, wait time at the facility for the healthcare service, and when the patient should not receive the healthcare service for other medical reasons. This notification may be outputted to the mobile device and displayed on the display when the location data of the mobile device is determined to be within the geofenced area that corresponds to the preventative healthcare facility. Alternatively, or in addition, the notification may include a voice message that may include the above-mentioned information.

Figure 8:
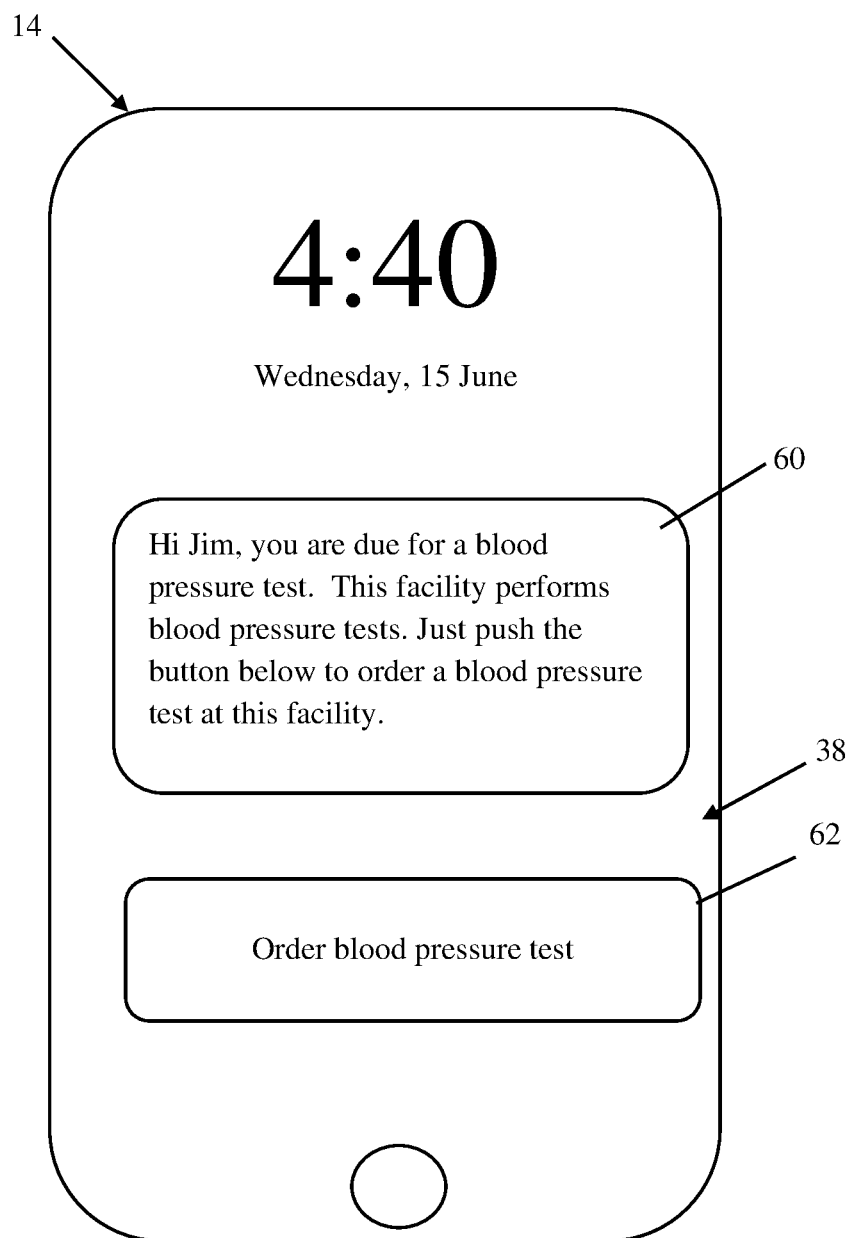
FIG. 8 is a schematic front view of mobile device displaying another message and message button on the display of the mobile device of the system according to FIG. 1.
Figure 9:
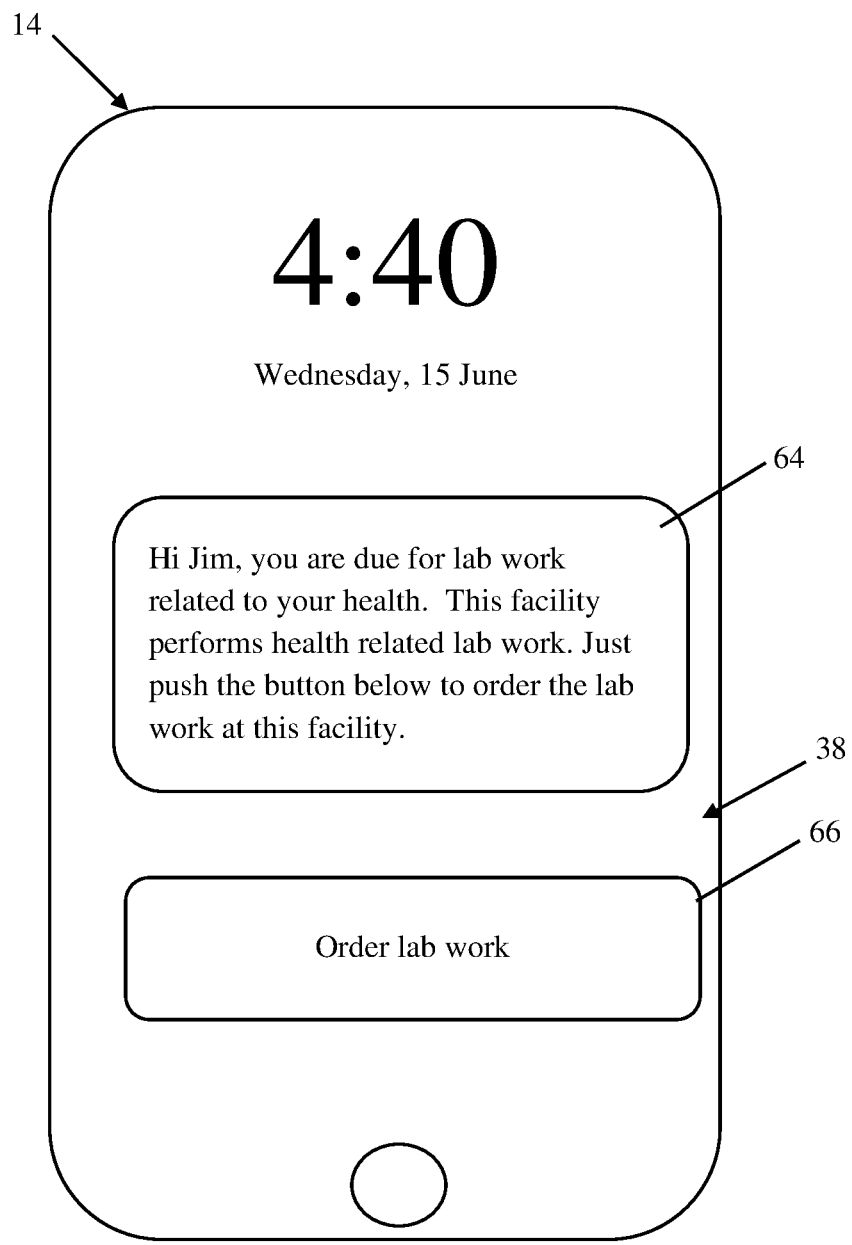
FIG. 9 is a schematic front view of mobile device displaying another message and message button on the display of the mobile device of the system according to FIG. 1.
Figure 10:
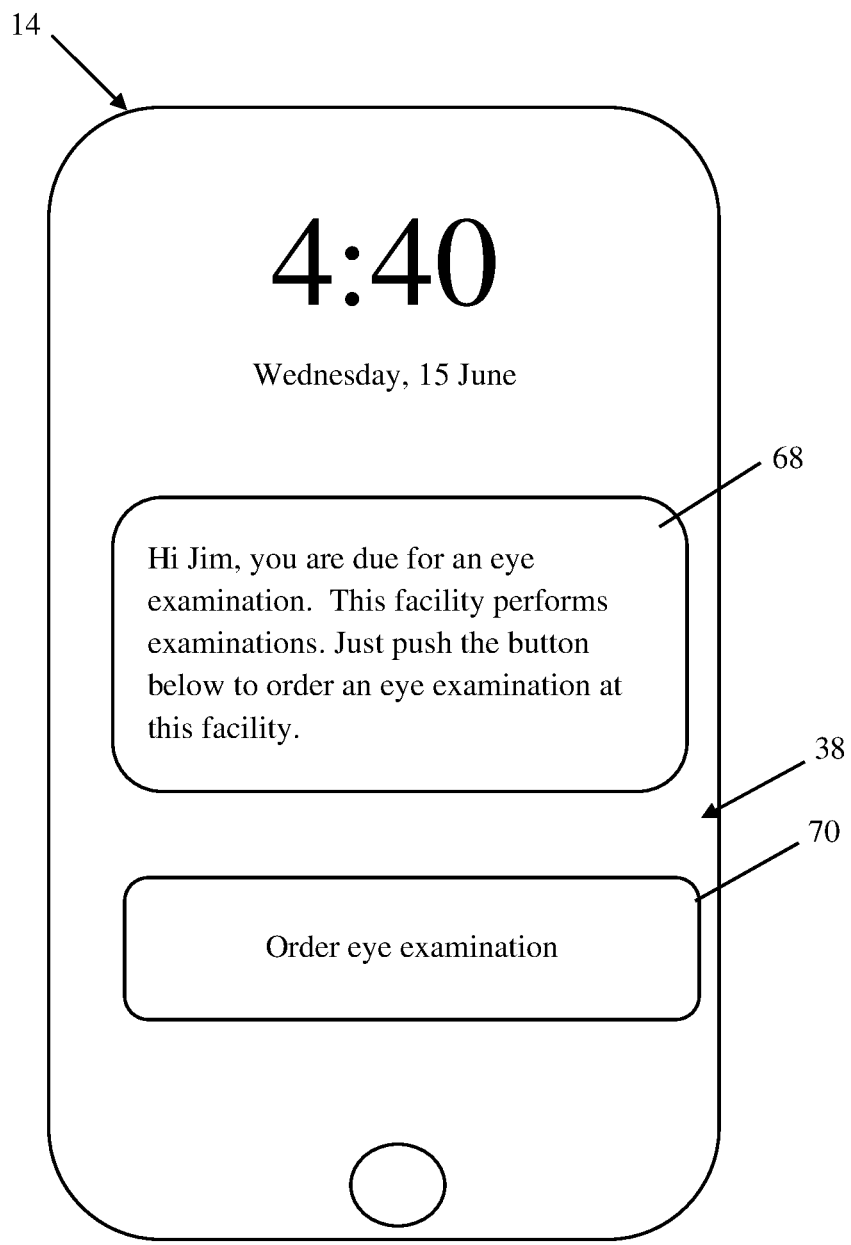
FIG. 10 is a schematic front view of mobile device displaying another message and message button on the display of the mobile device of the system according to FIG. 1.

The notification may include a message that the particular healthcare service is due for the patient and also prompt the patient to place an order for the particular healthcare service as show in FIGS. 8-10. For example, the message 60 may be that the healthcare service is providing blood pressure testing and also prompt the patient to request or place an order for the patient to have his or her blood pressure tested at the facility 31 by pressing a button 62 as shown in FIG. 8. The message 64 may be that the healthcare service may be providing lab work for the patient's physical examination and also prompt the patient to request or place an order for the lab work by pressing a button 66 as shown in FIG. 9. The message 68 may be that the healthcare service is providing eye examinations and also prompt the patient to request or place an order for the patient to have his or her eye examined at the facility 31 by pressing a button 70 as shown in FIG. 10. This notification may be outputted to the mobile device 14 and displayed on the display 38 when the location data of the mobile device is determined to be within the geofenced area that corresponds to the preventative healthcare facility 31. Alternatively, or in addition, the notification may include a voice message that may include the above-mentioned information.

Figure 3:
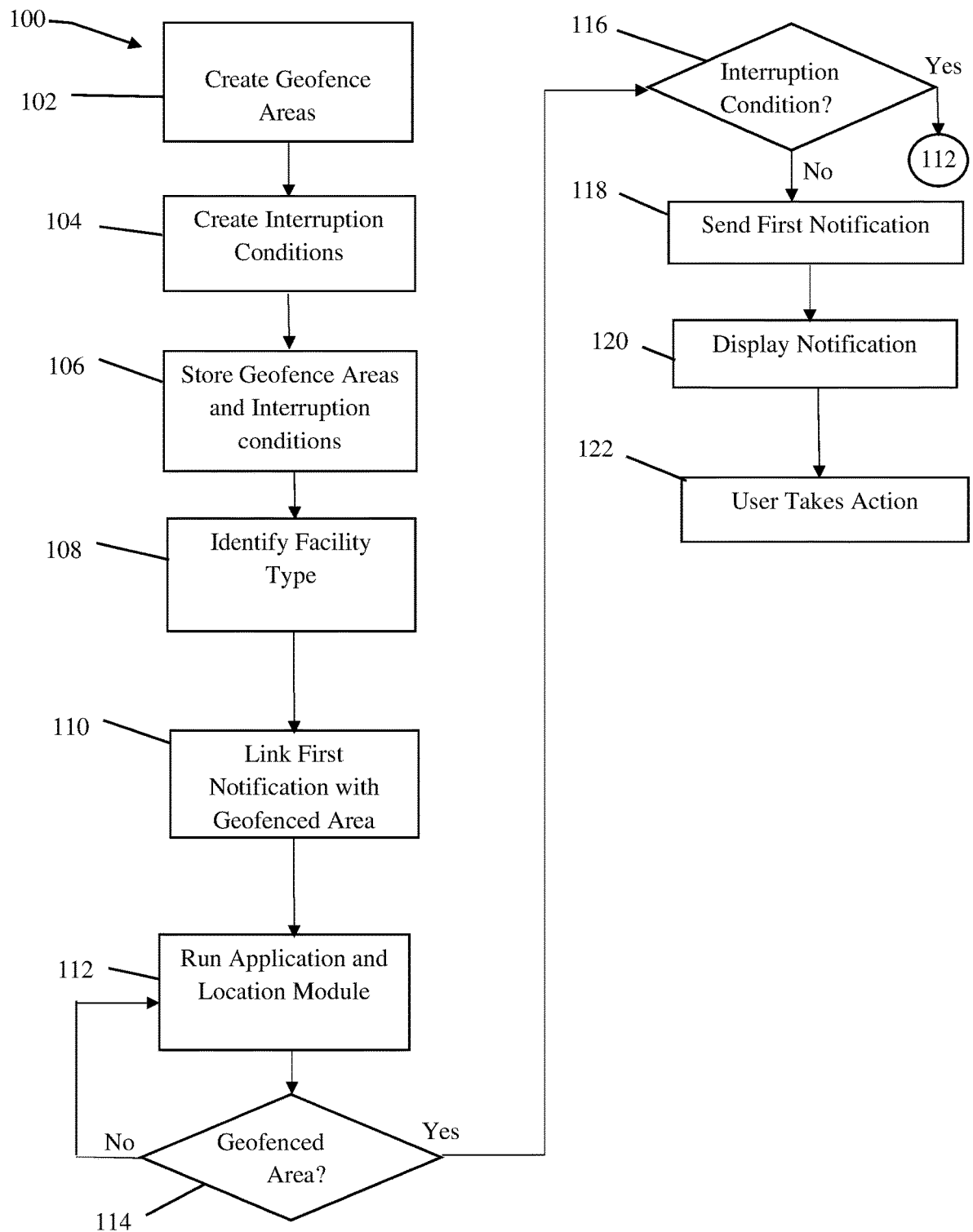
FIG. 3 is a flow diagram of an exemplary method according to FIG. 1.

With reference now to FIG. 3, an example methodology 100 is illustrated and described. While the methodology is described as being a series of acts or steps that are performed in a sequence, it is to be understood that the methodology is not limited by the order of the sequence. For instance, some acts or steps may occur in a different order than what is described herein. In addition, a step may occur concurrently with another step. Furthermore, in some instances, not all steps may be required to implement a methodology described herein.

Moreover, the steps or acts described herein may be computer-executable instructions that can be implemented by one or more processors and/or stored on a computer-readable medium or media. The computer-executable instructions may include a routine, a sub-routine, programs, a thread of execution, and/or the like. Still further, results of acts of the methodology may be stored in a computer-readable medium, displayed on the display device, and/or the like.

Figure 6:
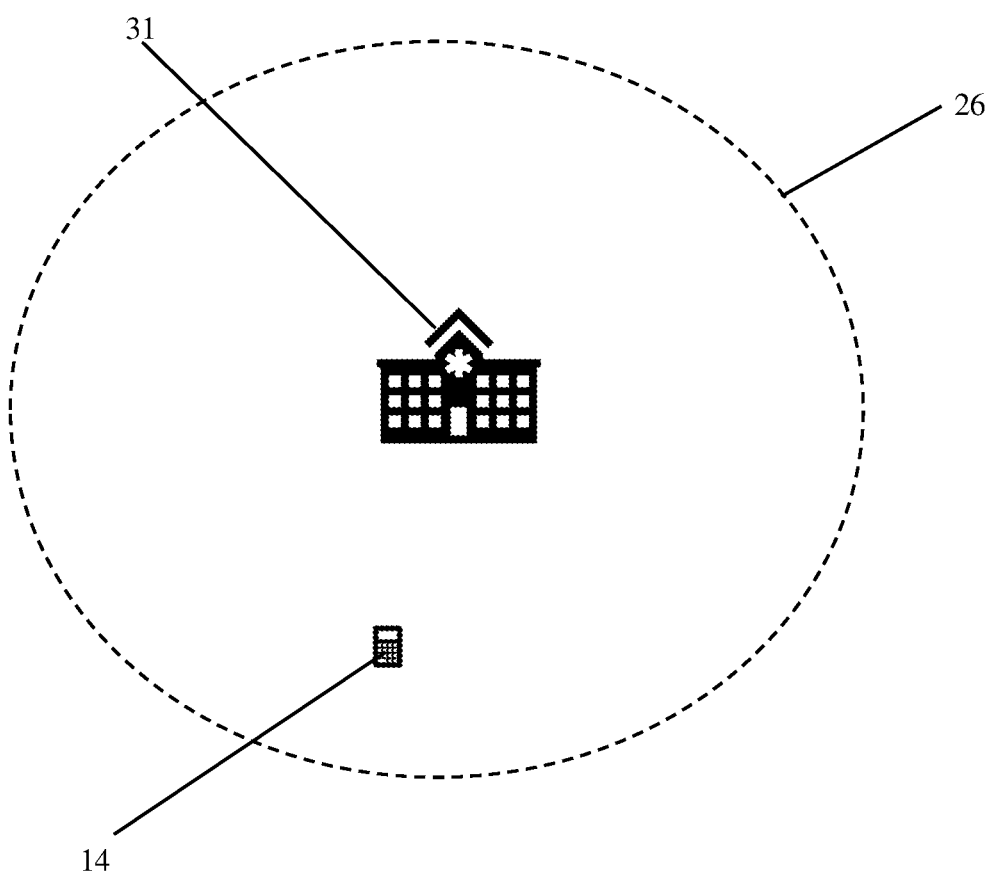
FIG. 6 is a schematic view of a healthcare facility surrounded by a geofence area associated with a healthcare facility and illustrating a mobile device located within the geofenced area according to the present invention.

In each step of this sequence of client-server message exchanges, a computer may process a request and return data. In step 102, the geofenced areas are created using the mapping module 24 based on data in the data store 30. One or more of the geofenced areas created may correspond to or be associated with the mobile device 14 associated with the patient and a location that has the facility 31. The facility 31 may offer one or more preventative healthcare services or one or more healthcare services. For example, one geofenced area 26 may be created for the facility 31 as shown in FIG. 6. In another example, a first group of geofenced areas 26a-26d may be created to correspond to the facility 31 as shown in FIG. 7. For example, a location such as an emergency room or an area that screens for cancer on a hospital campus may have several geofenced areas, since one large geofenced area encircling that location would not work, because there may be too many false triggers for people going to the hospital for other purposes. Further, there may be cases where there are one or more parking lots, driveways or entrances that are exclusively for that location, so these parking lots and other such locations would be associated with a geofenced area for that location.

In step 104, the interruption conditions for preventing the outputting of the notification when the location data of the mobile device is determined to be within the geofenced area may be created using the mapping module 24. In step 106, the geofenced areas and any interruption conditions are stored in the data store. In step 108, the facility may be identified. For example, the facility 31 stored may be identified as a hospital, free-standing emergency, urgent care, or walk-in clinic and other information related to that facility. In step 110, a first predetermined notification stored in the data store 30 or in the memory of the mobile device 14 may be linked with the one or more geofenced areas of the facility 31. This notification may include messages with information about one of or any combination of: that the location offers at least one healthcare service that can be received on an unscheduled basis, where in the facility that the at least one healthcare service is offered, whether or not the healthcare service is covered by the patient's insurance, the cost of the healthcare service, the out-of-pocket cost by the patient of the healthcare service, wait time at the facility for the healthcare service, and when the patient should not receive the healthcare service for other medical reasons.

Alternatively or in addition, the notification may include a message that the particular healthcare service is due for the patient and also prompt the patient to place an order for the particular healthcare service. For example, the healthcare service may be providing lab work for the patient's physical examination. The healthcare service may be testing the blood pressure of the patient. The healthcare service may be providing an eye examination of the patient. This notification may be outputted to the mobile device and displayed on the display when the location data of the mobile device is determined to be within the geofenced area that corresponds to the preventative healthcare facility. The notification may further include an invitation or suggestion to initiate a video or audio call to a qualified person that can help the patient regarding the situation.

In step 112, the mobile device 14 is turned on with the notification application 46 launched and running and the location module 34 running so that the system 10 receives location data of the mobile device 14. In step 114 the notification application 46 determines when the mobile device 14 is located within a geofenced area associated with the facility 31 stored in the data store 30. This may occur during an unscheduled visit to the healthcare facility by the patient. If the mobile device 14 is located within the geofenced area, then the system 10 may check in step 116 whether there is an interruption condition for that geofenced area. If there is an interruption condition, no notification is outputted to the mobile device 14 and the method goes back to step 112 to continue to receive location data of the mobile device 14.

If the mobile device 14 is located within the geofenced area and there is no interruption condition, then in step 118, the messaging system 32 sends the first predetermined notification to the mobile device 14 or the predetermined notification is retrieved from the memory of the mobile device 14. In step 120, the notification is displayed on the display 38 of the mobile device 14. The notification may include a message button 50 to give the option to place an audio or video call with a qualified healthcare professional an invitation or suggestion to initiate a video or audio call to a qualified person that can help the patient regarding the unscheduled visit. The message may also prompt the patient to request or place an order for the particular healthcare service. Alternatively or in addition, other ways to output the message may be provided such as an audio message outputted through the speakers of the mobile device. In step 122, the user may take action based on the displayed message(s).

Figure 5:
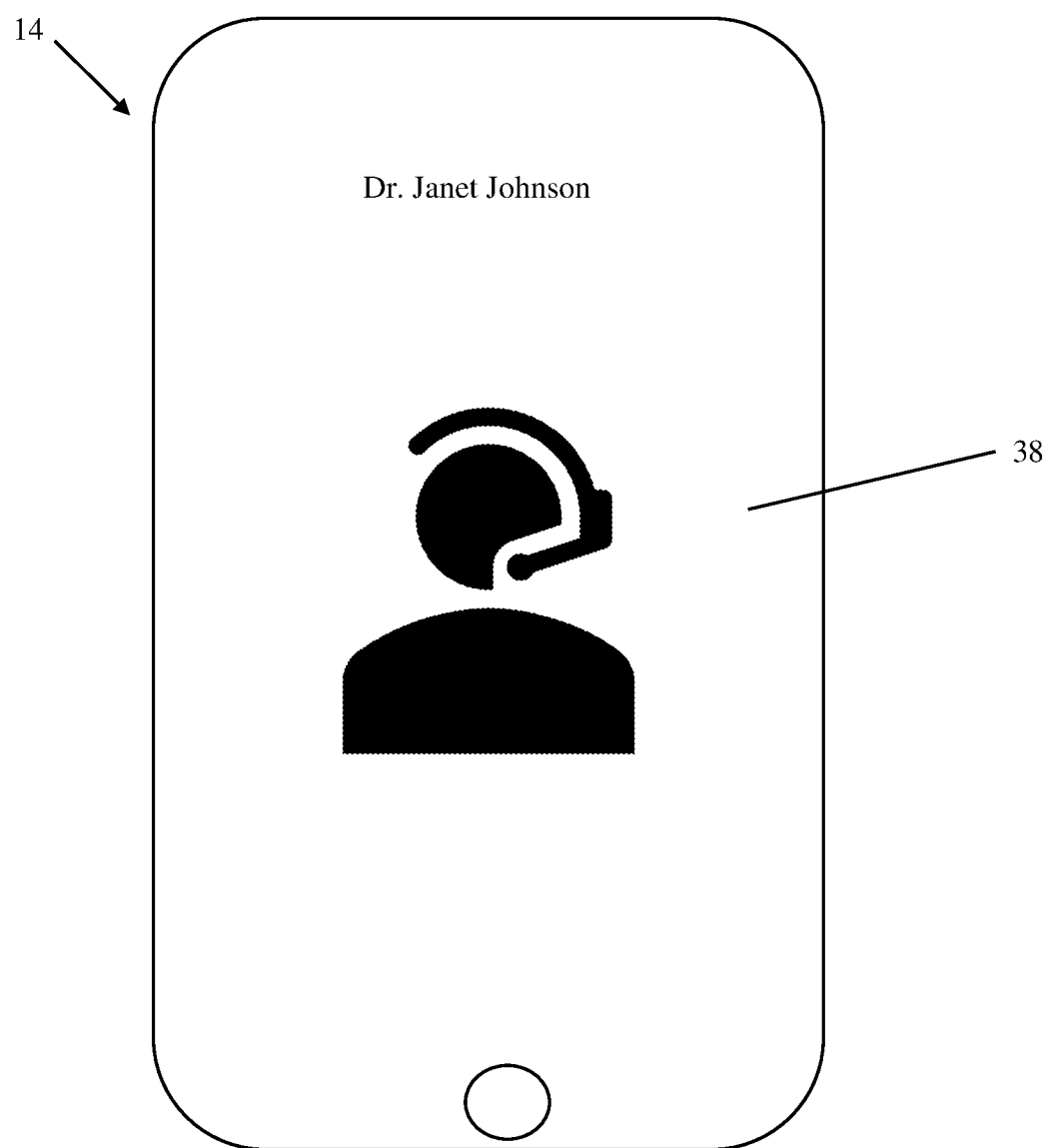
FIG. 5 is a schematic front view of mobile device displaying an image of a video call initiated by the user on the mobile device of the system according to FIG. 1.

For example, FIGS. 8-10 shows a message that a particular type of healthcare service is due and prompts the patient to order the healthcare service. In FIG. 8, the message 60 notifies the patient that their blood pressure test is due and that this particular facility 31 performs blood pressure tests. The message 60 also prompts the patient to order the blood pressure test and displays a button 62 that the patient can press to order the blood pressure test at the facility 31. In FIG. 9, the message 64 notifies the patient that lab work related to their health is due and that this particular facility 31 performs health related lab work. The message 64 also prompts the patient to order the blood pressure test and displays a button 66 that the patient can press to order that their lab work be performed for them at the facility 31. In FIG. 10, the message 68 notifies the patient that their eye examination is due and that this particular facility 31 performs eye examinations. The message 68 also prompts the patient to order the eye examination and displays a button 70 that the patient can press to order the eye examination at the facility 31. The message may also have a button to place a video or audio call to a doctor or other qualified professional that can help the patient regarding the visit as illustrated in FIG. 5. The method may also include enabling the user to cancel the notification without placing the call or taking further action.

FIG. 4 shows another example of a notification message and a message button generated by the messaging system 32 when the mobile device 14 enters the first geofenced area 26a associated with a free-standing emergency facility. If the user presses the message button 50 on the display 38, a video call will be placed with a doctor or other qualified professional that can help the patient regarding the unscheduled visit as illustrated in FIG. 5. The medical professional may be a doctor, physician assistant, nurse practitioner, or other medically or non-medically trained service provider who may provide information, service or support to the patient and can help the patient regarding the unscheduled visit. The method may also include enabling the user to cancel the notification without placing the call or taking further action.

In one example, a video call may be placed with a doctor to determine whether or not the injury requires going to an emergency medical facility. For certain injuries, the doctor may ask the patient to take a photograph of the injury using the mobile device and send the photograph to the doctor by email, text, or other suitable mode. Upon analyzing the photograph, the doctor may determine that the injury does not require the services of an emergency healthcare facility. The doctor may operate the computer to search the data store 30 and find an urgent care facility near the patient's location based on the mobile phone location and then suggest to the patient to go to the less costly urgent care facility, since the injury does not require use of an emergency healthcare facility.

The system and method reminds and encourages patients to seek preventative healthcare or other unscheduled healthcare services when they are in the vicinity of a facility that offers such care. The system and method conveniently notifies the patient when they are in the vicinity of the facility and provides further information to the patient to help the patient make a decision as to whether to use the facility to perform the healthcare service. The system and method may also prevent notifying the patient when they are in the vicinity of the location based on certain conditions.

The system and method also provides information quickly and conveniently to patients who seek immediate medical attention when they are approaching a healthcare facility and also to the medical professions involved with the patient, which also saves costs and time to diagnose and treat the medial condition of the patient and process the medical information. Although various embodiments of the disclosed system and method for providing notifications to a user based upon the user's location have been shown and described, modifications may occur to those skilled in the art upon reading the specification. The present application includes such modifications and is limited only by the scope of the claims.

What is claimed is:

1. A computer-implemented method for providing notifications and communication based on a patient entering into a geofenced area around a facility that offers healthcare services, the method comprising the following operations performed by at least one computer processor:
   a) creating a geofenced area associated with a mobile device and a location that has the facility, wherein the patient is associated with the mobile device;
   b) storing the geofenced area in a data store;
   c) determining when the mobile device has crossed or entered the geofenced area;
   d) sending a notification to the mobile device, wherein the notification includes a message that the particular healthcare service is due for the patient, wherein the notification further includes prompting the patient to request or place an order for the particular healthcare service by displaying an order button on a display of the mobile device that communicates to the user that the order button is for ordering the particular healthcare service by pressing the order button;
   e) outputting the notification to the mobile device when the location data of the mobile device is determined to be within the geofenced area that corresponds to the facility;
   f) prior to outputting the notification to the mobile device, determining if the patient had the at least one healthcare service within a predetermined time ago and preventing the outputting of the notification upon determining that the patient had the at least one healthcare service within a predetermined time ago; and
   g) prior to outputting the notification to the mobile device, determining that the at least one healthcare service should not be provided to the patient based on one or more insurance claims of the patient and preventing the outputting of the notification upon determining that the at least one healthcare service should not be provided to the patient based on one or more insurance claims of the patient,
   wherein the notification includes that the location offers the at least one healthcare service that can be received on an unscheduled basis, wherein the notification includes whether or not the at least one healthcare service is covered by the patient's insurance.

2. The computer-implemented method of claim 1, wherein the healthcare service is providing lab work for the patient's physical.

3. The computer-implemented method of claim 1, wherein the healthcare service is testing the blood pressure of the patient.

4. The computer-implemented method of claim 1, wherein the healthcare service is providing an eye examination of the patient.

5. The computer-implemented method of claim 1, further comprising:
   h) storing information as to when the particular healthcare service is due for the patient in the data store; and
   i) displaying on another display of a computer the information as to when the particular healthcare service is due, wherein the computer communicates with the mobile device via a computer network, wherein the computer is accessible by a person who provides information, service or support to the patient.

6. The computer-implemented method of claim 1, wherein the notification includes where in the location the at least one healthcare service is offered.

7. The computer-implemented method of claim 1, wherein the notification includes the wait time at the facility for the at least one health care service.

8. A non-transitory computer-readable storage medium storing executable instructions for providing notifications and communication to a patient based on a patient entering into a geofenced area around a facility that offers healthcare services, that, as a result of being executed by one or more processors of a computer system, cause the computer system to at least:

a) create a geofenced area associated with a mobile device and a location that has the facility, wherein the patient is associated with the mobile device;
b) store the geofenced area in a data store;
c) determine when the mobile device has crossed or entered the geofenced area;
d) sending a notification to the mobile device, wherein the notification includes a message that the particular healthcare service is due for the patient, wherein the notification further includes prompting the patient to request or place an order for the particular healthcare service by displaying an order button on a display of the mobile device that communicates to the user that the order button is for ordering the particular healthcare service by pressing the order button;
e) output the notification to the mobile device when the location data of the mobile device is determined to be within the geofenced area that corresponds to the facility;
f) prior to outputting the notification to the mobile device, determine if the patient had the at least one healthcare service within a predetermined time ago and preventing the outputting of the notification upon determining that the patient had the at least one healthcare service within a predetermined time ago; and
g) prior to outputting the notification to the mobile device, determine that the at least one healthcare service should not be provided to the patient based on one or more insurance claims of the patient and preventing the outputting of the notification upon determining that the at least one healthcare service should not be provided to the patient based on one or more insurance claims of the patient,
wherein the notification includes that the location offers the at least one healthcare service that can be received on an unscheduled basis, wherein the notification includes whether or not the at least one healthcare service is covered by the patient's insurance.

9. The non-transitory computer-readable storage medium of claim 8, wherein the notification includes that the location offers the at least one healthcare service that can be received on an unscheduled basis.

10. The non-transitory computer-readable storage medium of claim 8, wherein the notification includes where in the location the at least one healthcare service is offered.

11. The non-transitory computer-readable storage medium of claim 8, wherein the notification includes one of or both the cost of the at least one healthcare service and the out-of-pocket cost by the patient of the at least one healthcare service.

12. The non-transitory computer-readable storage medium of claim 8, wherein the notification includes the wait time at the facility for the at least one health care service.

13. The non-transitory computer-readable storage medium of claim 8, wherein the notification includes when the patient should not receive the at least one healthcare service for other medical reasons.

14. The non-transitory computer-readable storage medium of claim 8, further comprising prior to outputting the notification to the mobile device, determining that the at least one healthcare service should not be provided to the patient and preventing the outputting of the notification upon determining that the at least one healthcare service should not be provided to the patient.

15. The non-transitory computer-readable storage medium of claim 14, wherein determining that the at least one healthcare service should not be provided to the patient is based on the medical history of the patient.

16. The non-transitory computer-readable storage medium of claim 8 to further cause the computer system to at least prior to outputting the notification to the mobile device, determine that the preference of the patient is to not output the notification and preventing the outputting of the notification upon determining that the preference of the patient is to not output the notification.

17. The non-transitory computer-readable storage medium of claim 8 to further cause the computer system to at least prior to outputting the notification to the mobile device, determining that the at least one healthcare service is not in the insurance network of the patient and preventing the outputting of the notification upon determining that the at least one healthcare service is not in the insurance network of the patient.

18. The non-transitory computer-readable storage medium of claim 8 to further cause the computer system to at least prior to outputting the notification to the mobile device, determining that the cost of the at least one healthcare service is not available or more than a predetermined amount at the facility and preventing the outputting of the notification upon determining that the cost of the at least one healthcare service is not available or more than a predetermined amount at the facility.

19. A system for providing notifications and communication to a patient based on a patient entering into a geofenced area around a facility that offers healthcare services comprising:
one or more processors; and one or more memories coupled to the one or more processors, the one or memories having stored therein processor executable instructions which when executed by any set of the one or more processors, perform a process comprising:
creating a geofenced area associated with a mobile device and a location that has the facility, wherein the patient is associated with the mobile device;
storing the geofenced area in a data store;
determining when the mobile device has crossed or entered the geofenced area;
sending a notification to the mobile device, wherein the notification includes a message that the particular healthcare service is due for the patient, wherein the notification further includes prompting the patient to request or place an order for the particular healthcare service by displaying an order button on a display of the mobile device that communicates to the user that the order button is for ordering the particular healthcare service by pressing the order button;
outputting the notification to the mobile device when the location data of the mobile device is determined to be within the geofenced area that corresponds to the facility;
prior to outputting the notification to the mobile device, determining if the patient had the at least one healthcare service within a predetermined time ago and preventing the outputting of the notification upon determining that the patient had the at least one healthcare service within a predetermined time ago; and
prior to outputting the notification to the mobile device, determining that the at least one healthcare service should not be provided to the patient based on one or more insurance claims of the patient and preventing the outputting of the notification upon determining that the at least one healthcare service should not be provided to the patient based on one or more insurance claims of the patient, wherein the notification includes that the location offers the at least one healthcare service that can be received on an unscheduled basis, wherein the notification includes whether or not the at least one healthcare service is covered by the patient's insurance.

\* \* \* \* \*